United States Patent [19]
Young et al.

[11] Patent Number: 4,564,360
[45] Date of Patent: Jan. 14, 1986

[54] ADJUSTABLE DOSE INJECTION PISTOL

[75] Inventors: David M. Young, Loughborough; Andrew W. Blower, Ashby-de-la-Zouch, both of England

[73] Assignee: Fisons plc, Ipswich, England

[21] Appl. No.: 536,744

[22] Filed: Sep. 28, 1983

[30] Foreign Application Priority Data

Oct. 8, 1982 [GB] United Kingdom ............... 8228809

[51] Int. Cl.⁴ .............................................. A61D 7/00
[52] U.S. Cl. ................................................... 604/183
[58] Field of Search ...................... 604/68, 70, 71, 183, 604/186

[56] References Cited

U.S. PATENT DOCUMENTS

| | | | |
|---|---|---|---|
| 2,714,887 | 8/1955 | Venditty | 604/68 |
| 2,928,390 | 3/1960 | Venditty et al. | 604/71 X |
| 3,353,537 | 11/1967 | Knox et al. | 604/186 X |
| 3,400,716 | 9/1968 | Schultz | 604/186 X |
| 3,406,684 | 10/1968 | Tsujino | 604/70 |
| 3,682,175 | 8/1972 | Halter | 604/186 X |
| 3,714,943 | 2/1973 | Yanof et al. | 604/71 X |
| 3,952,919 | 4/1976 | Hansen et al. | 604/183 X |
| 4,033,346 | 7/1977 | Phillips et al. | 604/186 X |

Primary Examiner—C. Fred Rosenbaum
Assistant Examiner—Christa K. Scott
Attorney, Agent, or Firm—Marshall, O'Toole, Gerstein, Murray & Bicknell

[57] ABSTRACT

There is described an adjustable dose injection pistol comprising a body assembly (1) including an elongate chamber (8), a piston chamber (3) including a piston (13) slideable in the chamber (8) between filled and discharged positions and means for adjusting (16, 26, 19, 20, 22, 23) one of said positions.

The means comprise a selectable plurality of channels (20, 22, 23) included in one of the assemblies (1, 3), the channels (20, 22, 23) being spaced about and parallel to the piston-chamber axis, and an arrestor (19) located on the other assembly (1, 3), the arrestor (19) being selectably engageable with an aligned channel (20, 22, 23) upon movement of said piston (13) between said positions.

The channels (20, 22, 23) are preferably located in the piston assembly (3) on a sleeve (16) concentrically mounted with the piston (13) and rotable with respect to the chamber (8).

The pistol may be used for the injection of liquids into animals.

14 Claims, 5 Drawing Figures

ADJUSTABLE DOSE INJECTION PISTOL

This invention relates to an adjustable dose injection pistol.

Injection devices, in the form of pistols, for the administration of liquid medicaments to animals are well known, from for example United Kingdom Pat. No. 1464773 and French Pat. No. 2272688. Conventionally, these devices comprise a body having an elongate chamber, a piston slidable in the chamber between filled and discharged positions, a chamber outlet, for discharging liquid from the chamber, a first handle for enabling the body to be held in the hand of an operator and a second handle connected to the piston, and positioned for cooperation with the first handle to enable the handles to be squeezed together to move the piston from the filled position to the discharged position.

A large number of adjustable injection pistols have been described which are capable of administering metered doses. Several different methods have been proposed for metering the dose in such devices. For example, UK Pat. No. 733168 discloses a device in which the filled position of the piston within the chamber is controlled by the adjustment of a screw located on the second handle which limits the motion of the second handle with respect to the first, and so regulates the size of the dose discharged on squeezing the handles together.

UK patent application No. 2083567A discloses a device in which the filled position of the piston is regulated by adjustment of a micrometer screw guage located in the handle assembly.

The devices disclosed in UK Pat. No. 733168 and UK patent application No. 2083567A suffer from the disadvantage that they are both difficult to adjust and difficult to clean after use.

U.S. Pat. No. 3,110,310 and French Pat. No. 2236477 both disclose devices in which the dose discharged is regulated by an irregularly shaped metering plate on the second handle which limits the discharge stroke of the piston by interaction with the body of the device. German Pat. No. 730971 relates to a device in which the discharge stroke of the piston is controlled by an adjustable device located on the piston. These three devices suffer from the disadvantage that they are also difficult to adjust and that the selected dose can be accidentally altered during actuation.

Other metering methods are known in non-pistol type of injection devices, such as syringes. Thus French Pat. No. 711644 discloses a syringe in which the filled position of the piston is regulated by interaction of an arrestor attached to the piston with a set of selectable parallel slots of different length on the syringe body. This device suffers from the disadvantage that it can not readily be adjusted with one hand, and that it lacks robustness.

We have now found an improved form of adjustable dose injection pistol.

According to the invention we provide an adjustable dose injection pistol comprising a body assembly including an elongate chamber, a piston assembly including a piston slidable in the chamber between filled and discharged positions and means for adjusting one of said positions wherein the means comprise a selectable plurality of channels included in one of the assemblies, the channels being spaced about and parallel to the piston-chamber axis, and an arrestor located on the other assembly, the arrestor being selectably engagable with an aligned channel upon movement of said piston between said positions.

We prefer the channels to be located in the piston assembly, particularly in a sleeve concentrically mounted with the piston and rotatable with respect to the chamber.

We prefer one end of each channel to be open, terminating in a common plane transverse to the piston-chamber axis.

We prefer the arrestor to be capable of selectable engagement with each of the channels when the piston is in the discharged position, particularly the minimum volume position.

The channels are preferably spaced angularly about the piston-chamber axis. The length of each channel is preferably different to the lengths of other channels. The number of channels in the adjustment means depends on the particular requirements of the user of the device. One of the channels is preferably open at each end, to permit disengagement of the piston assembly from the body assembly.

The remaining channels may be used to limit the discharged, or preferably the filled position of the piston. When there are two such channels, we particularly prefer one channel to be a multiple, e.g. twice the length of the other, so that one dose discharged from the chamber may be a multiple, e.g. double the dose of the other.

We prefer a further selectable position to be provided which allows the piston to be locked when the device is not in use. Thus when the arrestor is capable of selectable engagement of the channels with the piston in the minimum volume position, the appropriate "lock" position may be a short channel which forms a substantially tight fit with the arrestor and limits motion of the piston with respect to the barrel along the piston-chamber axis. The body assembly includes an outlet for discharging liquid from the chamber and is preferably provided with a means for attaching a liquid reservoir and an inlet for delivering liquid from the reservoir to the chamber. The inlet and outlet are preferably controlled by appropriate one way valves. The inlet and outlet may communicate with the chamber at different, or preferably the same position.

A hypodermic needle may be attached to the body assembly, communicating with the chamber via the outlet by conventional means.

According to a preferred form of the invention there is provided an adjustable dose injection pistol comprising a body assembly including an elongate chamber, means for attaching a liquid reservoir, an inlet for delivering liquid from the reservoir to the chamber and an outlet for discharging liquid from the chamber, a piston assembly including a piston slidable in the chamber between maximum and minimum volume positions, a first handle for enabling the body assembly to be held in the hand of an operator, a second handle connected to the piston assembly and positioned for cooperation with the first handle to enable the handles to be squeezed together to move the piston between said positions, and means for adjusting the maximum volume position of the piston, wherein the adjustment means comprise a selectable plurality of channels located in a sleeve concentrically mounted with the piston and rotatable with respect to the chamber, the channels being spaced angularly about and parallel to the piston-chamber axis, one end of each channel being open and terminating in a common plane transverse to the piston-chamber axis, the length of each channel being different from the lengths of other channels, and an arrestor located in the body assembly, the arrestor being selectably engagable when the piston is in the minimum volume position with an aligned channel upon movement of said piston between said positions.

An embodiment of the invention will now be described by way of example only, with reference to the accompanying drawings, in which.

Figure 1:
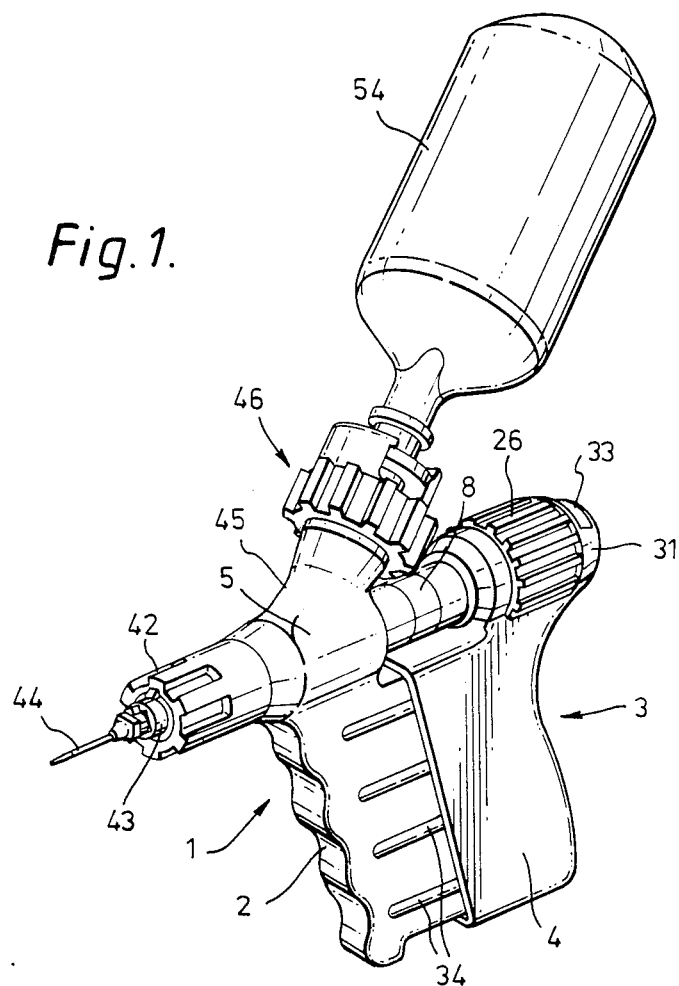
FIG. 1 is a perspective view of an adjustable dose injection pistol according to the invention with a liquid reservoir mounted thereon.

Referring to the drawings the pistol comprises a body assembly 1 having a cast body handle 2 of the pistol grip type and a piston assembly 3, including a piston handle 4 positioned to cooperate with, and slide over the body handle 2, on squeezing the grip by hand.

The body assembly 1 has in its upper portion a cylindrical mounting 5 within which is fitted an elongate valve assembly 6. The valve assembly 6 communicates at one end with a needle attachment assembly 7, and at the other end with an elongate chamber in the form of a barrel 8, the needle attachment assembly 7, valve assembly 6 and barrel 8 lying on a common, piston-barrel, axis. The barrel 8 is sealed against the valve assembly 6 by a barrel O-ring 9 and an internally threaded barrel cap 10, which screwably engages with the valve assembly 6. The barrel 8 is provided with a peripheral flange 11 at one end, which is engaged by a corresponding internal peripheral flange 12 in the barrel cap 10.

The piston assembly 3 comprises a piston 13, mounted in the barrel 8 and sealed against the walls of the barrel 8 by a suitable seal illustrated as piston O-ring 14. The piston 13 is connected by a vaned rod 15 to a sleeve 16 comprising two sleeve body halves 16a and 16b, concentrically mounted with the piston 13, and rotatable about a rod end bearing 17 on the rod 15 which is accommodated by a corresponding recess 18 in the sleeve 16. The illustrated form of the piston 13, rod 15, and rod end bearing 17, in which the three components are a single moulded assembly is particularly favoured.

The sleeve 16 is mounted on the rod 15 so that it can slide over the barrel 8. The motion of the sleeve along the piston-barrel axis 16 is determined by the selectable engagement of an arrestor in the form of a detente 19, located on a lower side wall of the barrel 8 distant from the valve assembly 6, with a plurality of channels in the sleeve 16. In the injection pistol illustrated, there are four selectable positions in the form of three channels 20, 22 and 23, and a lock position 21, spaced angularly about and parallel to the piston-barrel axis.

One end of each channel 20, 22 and 23 is open and terminates in a common plane in the form of an annular groove 24 which is at right angles to the piston-barrel axis and in the rear portion of the sleeve 16 distant from the valve assembly 6. The groove 24 is of sufficient width and depth to accommodate the detente 19.

The other end of each channel terminates at a different distance from the groove 24. The length of each channel determines the distance that the sleeve 16 can move over the barrel 8, and thus limits the maximum filled position of the piston 13 within the barrel 8.

Channel 20 runs from the valve assembly end of the sleeve 16 to the groove 24, and allows the piston 13, and thus the piston assembly 3 to be disengaged from the barrel 8, and the body assembly 1.

Moving clockwise around the sleeve 16, from channel 20, viewing towards the valve assembly, the next selectable position is the lock position 21, which runs from the groove 24 a sufficient distance to just accommodate the detente 19. This has the effect of holding the piston 13 in a locked position in the barrel 8, thereby preventing accidental discharge of the pistol.

The channel 22 runs a sufficient distance from the groove 24 towards the valve assembly 6, to permit movement of the piston 13 to a first filled position. This first position preferably corresponds to half the operating volume of the barrel 8.

The channel 23 runs in a fashion corresponding to channel 22 to allow movement of the piston 13 to a second, further filled position. This second position preferably corresponds to the full operating volume of the barrel 8.

The movement of the sleeve 16 over the barrel 8 is biased away from the valve assembly 6 by the compression spring 25, mounted over the rod 15 within the sleeve 16.

Figure 2:
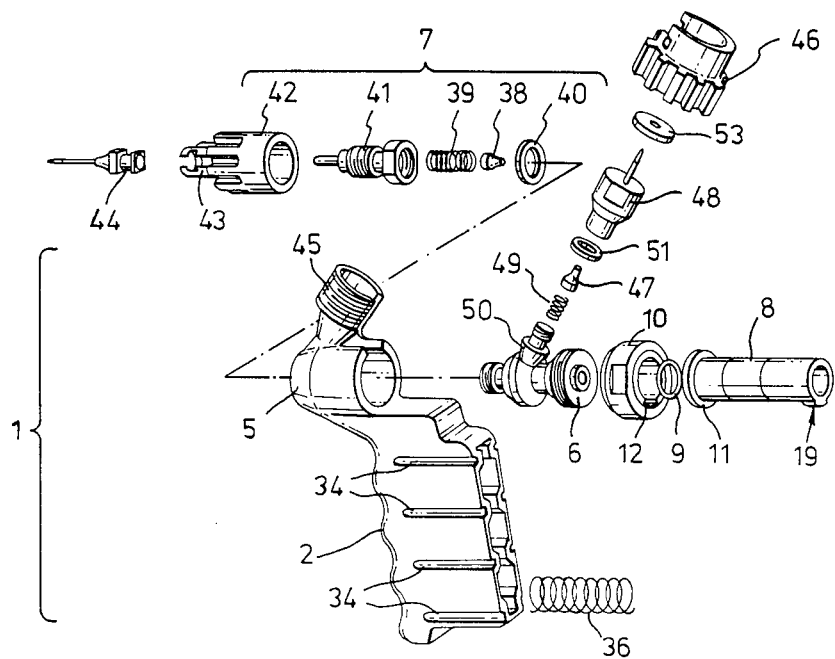
FIG. 2 is an exploded view illustrating the parts of the injection pistol in position for assembly.
Figure 2:
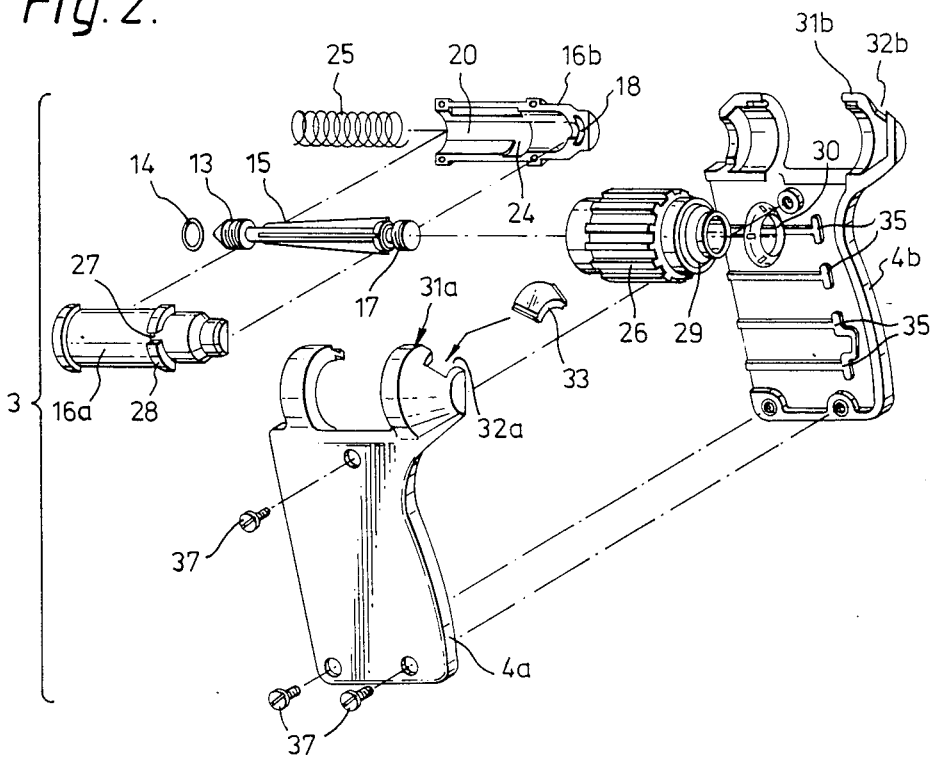

A knurled selector cylinder 26 is concentrically mounted with the rod 15, having a tight press fit with the rear portion of the sleeve 16. For ease of alignment on assembly, as shown in FIG. 2, the selector cylinder 26 has an internal rib (not shown), parallel to the piston-barrel axis which interacts with a corresponding recess 27 in a peripheral annular rib 28 on the body half 16a of the sleeve 16.

The rear portion of the selector cylinder 26 is provided with an inclined annular recess 29 into which is fitted an indication dial 30 which bears indicia to show which channel has been selected. The selector cylinder 26 is rotatably mounted in a cradle 31 formed by the two cradle halves 31a and 31b, at the upper portion of the piston handle halves 4a and 4b respectively. The upper portions of the piston handle halves 4a, 4b are also provided with recesses 32a, 32b which form a window frame 32, arranged to hold a window 33 through which the dial 30 can be viewed.

The abutting surfaces of the selector cylinder 26 and the cradle 31 may interact, e.g. by a "click" interaction, to bias the selector cylinder to align a selected position with the detente 19. A particularly preferred interaction is one in which the selector cylinder 26 is provided with projections on the periphery of the rear surface, corresponding to the selectable position 20, 21, 22 and 23, which interact with a complementary identation on the cradle 31.

In a preferred form, the lock position 21 does not extend beyond the groove 24, and the selection of the lock position 21, is indicated by a "click" interaction of the type described above.

The body handle 2 has on each exterior side four parallel grooves 34 arranged to cooperate with corresponding tongues 35 on the interior side of piston handle halves 4a, 4b. The piston assembly 2 is biased away from the body assembly 1 by the compression spring 36 located within the bottom pair of groove-tongue arrangements of the pistol grip formed by the handles 2 and 4.

The piston handle halves 4a, 4b are held together by means of three screws 37.

The needle attachment assembly 7 at the front of the injection pistol comprises a delivery valve 38 biased towards the valve assembly 6 by a compression spring 39, sealing the valve assembly 6 with the assistance of the ring washer 40. The front of the spring 39 is retained in a nozzle mount 41, which is held in place against the valve assembly 6 by a cylindrical needle mount 42, which engages the valve assembly 6 by a screw arrangement. The needle mount 42 is provided at the front end with a centrally placed hub 43 arranged to receive a Luer-type hypodermic needle 44.

The cylindrical mounting 5 on the body assembly 1 has a rearwardly inclined side arm portion 45, bearing a cylindrical retaining screw 46, within which a reservoir valve 47 is located. The reservoir valve 47 is biased to bear against a needle block 48 by a compression spring 49 supported by a rearwardly inclined sidearm 50 on the valve assembly 6 and sealed against the needle block 48 by a ring washer 51. The needle block 48 has a centrally mounted needle 52 on the upper portion, surrounded by a reservoir washer 53, which needle is arranged to communicate with a pierceable liquid reservoir 54 retained in the retaining screw 46 as shown in FIG. 1.

Figure 4:
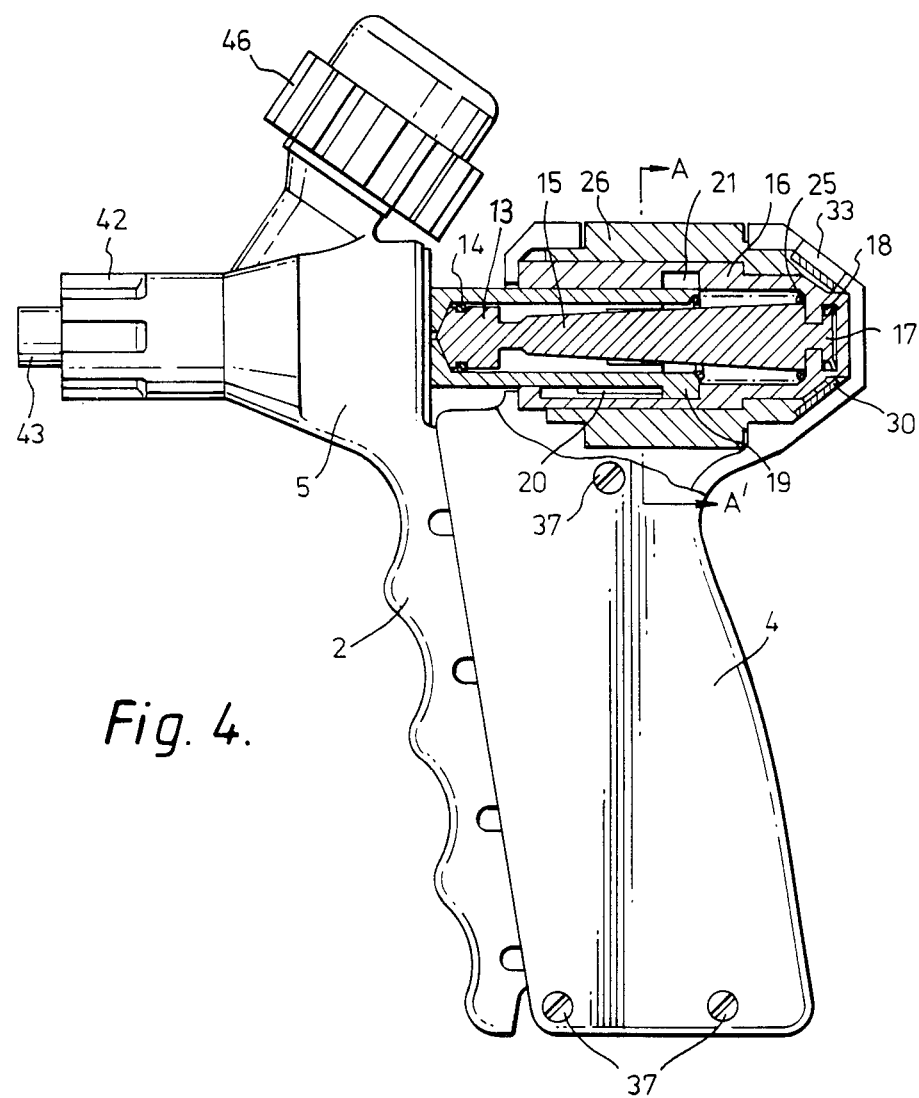
FIG. 4 is a schematic partial vertical section through the injection pistol when in a discharged position.
Figure 5:
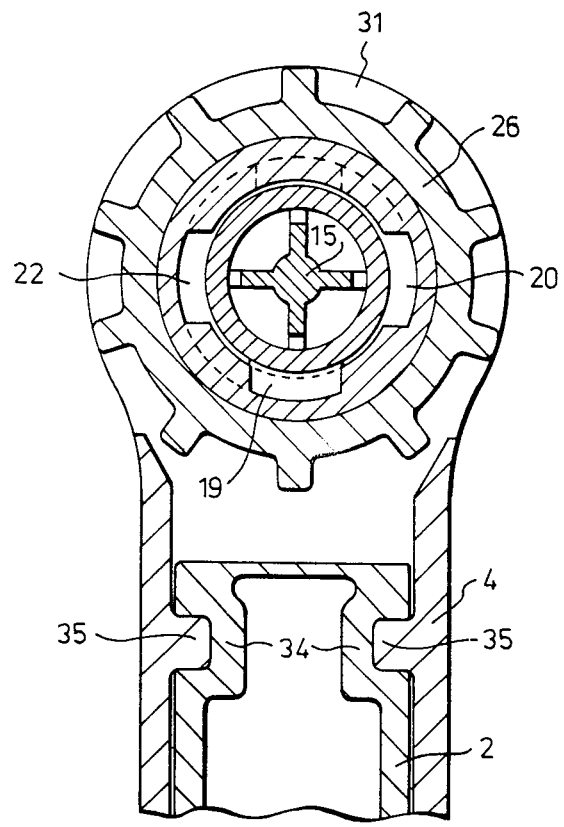
FIG. 5 is a cross-section along the line A-A' in FIG. 4.

In operation, the injection pistol is used in association with a hypodermic needle 44 and a liquid reservoir 54 as shown in FIG. 1. The dose of liquid to be delivered is selected by squeezing the body and pistol handles 2, 4 together as shown in FIG. 4. This brings the piston 13 into a minimum, discharged position in the barrel 8. A desired channel in the sleeve 16 is selected and aligned by rotating the knurled selector cylinder 26 until the appropriate position is indicated by the appropriate indicia on the indicator disc 30 appearing in the window 33. The detente 19 on the barrel 8 will now be aligned to engage with a selected channel. In the injection pistol illustrated, four alternative positions can be selected. The channel 20 permits the injection pistol to be dismantled or assembled.

The position 21 does not allow the piston 13 to move towards a fill position and corresponds to a lock position.

As described above, the channels 22 and 23 permit the selection of a half and full operating volume of the barrel 8, respectively.

Figure 3:
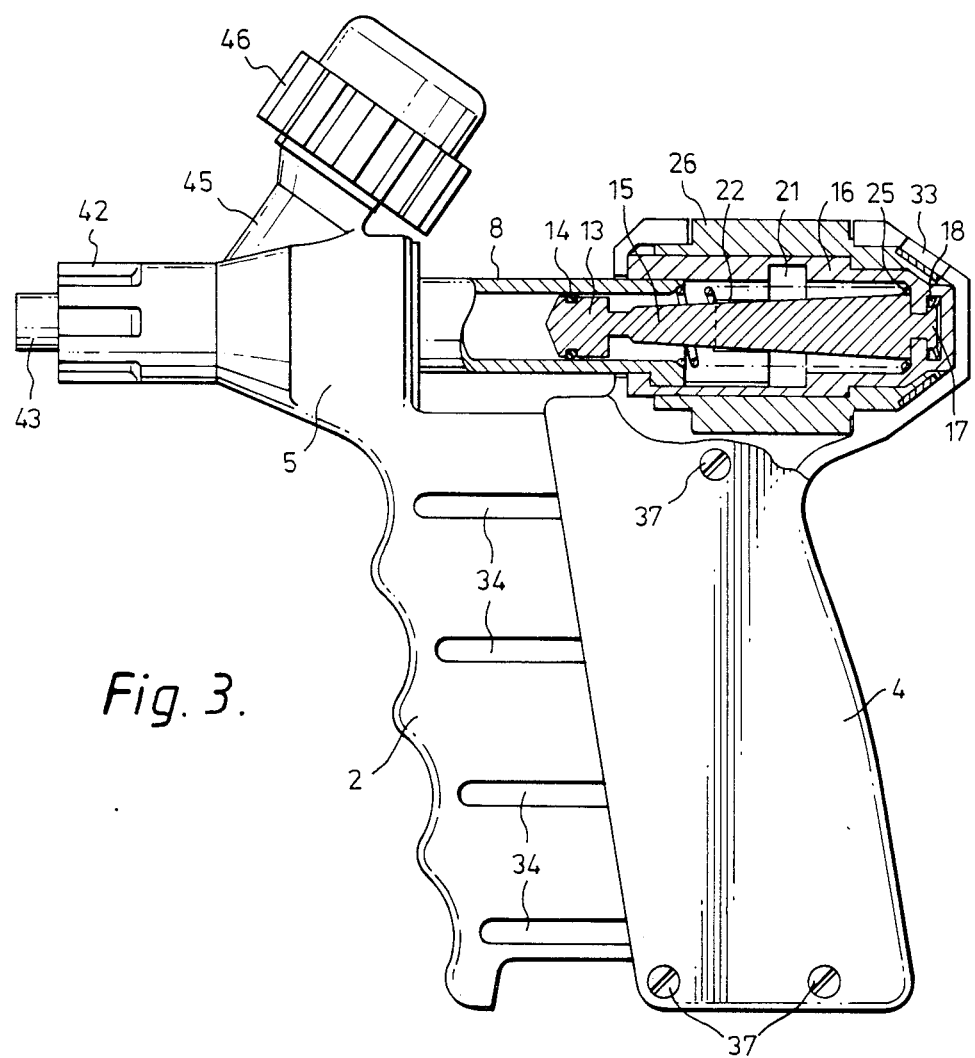
FIG. 3 is a schematic partial vertical section through the injection pistol when in a maximum filled position.

When channels 20, 22 or 23 are selected, on relaxing the hold on the handles 2, 4, the body assembly 1 will move away from the piston assembly 3, as shown in FIG. 3. When channel 22 or 23 is selected, and a liquid reservoir 54 is connected via the retaining screw 46, liquid will fill the barrel to a selected, predetermined volume, via the reservoir valve 47 and valve assembly 6. On squeezing handles 2, 4 together again, liquid will be discharged through the needle 44, via the valve assembly 6 and delivery valve 38. The pistol may be primed before use by holding in a horizontal position and squeezing together and releasing the handles until all air has been expelled from the syringe.

In a preferred form, the annular groove 24 is provided with a discontinuity, between channels 20 and 23, so that it is not possible to move the sleeve 16 from a fill position to a dismantle position.

It is, of course, possible to provide sleeves with more channels, allowing a greater number of alternative doses to be selected. Also, it is possible to use different barrel and pistons, e.g. a barrel and piston with a fifth the total operating volume of the standard fitting. Such additional components may be supplied in the form of a kit.

We claim:

1. An adjustable dose injection pistol comprising a body assembly including an elongate chamber, a piston assembly including a piston slidable in the chamber along a piston-chamber axis and being filled and discharged positions and means for adjusting one of said positions, wherein the means comprise a selectable plurality of channels included in one of the assemblies, the channels being spaced about and parallel to the piston-chamber axis, wherein one end of each channel is open and terminates in a common plane transverse to the piston-chamber axis, and an arrestor located on the other assembly, the arrestor being selectably engagable via the common plane with an aligned channel upon movement of said piston between said positions.

2. A pistol according to claim 1, wherein the channels are located in the piston assembly.

3. A pistol according to claim 1, wherein the channels are located in a sleeve concentrically mounted with the piston and rotatable with respect to the chamber.

4. A pistol according to claim 1, wherein the arrestor is capable of selectable engagement with each of the channels when the piston is in the discharged position.

5. A pistol according to claim 1, wherein the channels are spaced angularly about the piston-chamber axis.

6. A pistol according to claim 1, wherein the length of each channel is different to the lengths of other channels.

7. A pistol according to claim 1, wherein one channel is twice the length of another channel.

8. A pistol according claim 1, wherein one of the channels is open at each end, to permit disengagement of the piston assembly from the body assembly.

9. A pistol according to claim 1, wherein the adjustment means includes a selectable lock position which allows the piston to be locked.

10. A pistol according to claim 1, wherein the sleeve is provided with a biasing means capable of biasing the alignment of a selected channel or the lock position with the arrestor.

11. A pistol according to claim 10, wherein the biasing means is in the form of a click interaction.

12. A pistol according to claim 1 including an outlet, wherein the body assembly is provided with means for attaching a liquid reservoir and an inlet for delivering liquid from the reservoir to the chamber.

13. A pistol according to claim 12, wherein the inlet and outlet are controlled by appropriate one way valves.

14. An adjustable dose injection pistol comprising a body assembly including an elongate chamber, means for attaching a liquid reservoir, an inlet for delivering liquid from the reservoir to the chamber and an outlet for discharging liquid from the chamber,
  a piston assembly including a piston slidable in the chamber between maximum and minimum volume positions,
  a first handle for enabling the body assembly to be held in the hand of an operator,
  a second handle connected to the piston assembly and positioned for cooperation with the first handle to enable the handles to be squeezed together to move the piston between said positions, and means for adjusting the maximum volume position of the piston, wherein the adjustment means comprise a selectable plurality of channels located in a sleeve concentrically mounted with the piston and rotatable with respect to the chamber, the channels being spaced angularly about and parallel to the piston-chamber axis, one end of each channel being open and terminating a common plane transverse to the piston-chamber axis, the length of each channel being different from the lengths of other channels, wherein one end of each channel is open and terminates in a common plane transverse to the piston-chamber axis, an arrestor located in the body assembly, the arrestor being selectably engagable via the common plane when the piston is in the minimum volume position with an aligned channel upon movement of said piston between said positions.

* * * * *

UNITED STATES PATENT AND TRADEMARK OFFICE
CERTIFICATE OF CORRECTION

PATENT NO. : 4,564,360
DATED : January 14, 1986
INVENTOR(S) : David Mackay Young & Andrew William Blower It is certified that error appears in the above-identified patent and that said Letters Patent is hereby corrected as shown below:

In Claim 1, located at:
Column 6, line 12, the word "being" should be --between--.

Signed and Sealed this

Seventeenth Day of June 1986

[SEAL]

Attest:

DONALD J. QUIGG

Attesting Officer

Commissioner of Patents and Trademarks